(12) United States Patent
Huang

(10) Patent No.: US 9,056,049 B2
(45) Date of Patent: Jun. 16, 2015

(54) MICRO-PARTICLE COMPRISING A PROTEIN EXTRACT FROM SWEET POTATO FOR EXTENDING SATIETY AND CONTROLLING BLOOD GLUCOSE AND LIPID LEVELS

(71) Applicant: Chin Yuan Huang, Taipei (TW)

(72) Inventor: Chin Yuan Huang, Taipei (TW)

( * ) Notice: Subject to any disclaimer, the term of this patent is extended or adjusted under 35 U.S.C. 154(b) by 175 days.

(21) Appl. No.: 13/905,511

(22) Filed: May 30, 2013

(65) Prior Publication Data

US 2014/0356420 A1  Dec. 4, 2014

(51) Int. Cl.
| | |
|---|---|
| *A61K 36/39* | (2006.01) |
| *A61K 9/16* | (2006.01) |
| *A61K 9/20* | (2006.01) |
| *A61K 45/06* | (2006.01) |
| *A61K 38/16* | (2006.01) |
| *A61K 36/899* | (2006.01) |
| *A23L 1/305* | (2006.01) |
| *A23J 1/00* | (2006.01) |
| *A61K 9/46* | (2006.01) |

(52) U.S. Cl.
CPC .............. *A61K 9/167* (2013.01); *A61K 9/2086* (2013.01); *A61K 45/06* (2013.01); *A61K 36/39* (2013.01); *A61K 38/168* (2013.01); *A23V 2002/00* (2013.01); *A61K 36/899* (2013.01); *A61K 35/741* (2013.01); *A23L 1/3055* (2013.01); *A23J 1/006* (2013.01); *A61K 9/0007* (2013.01); *A61K 9/2077* (2013.01)

(58) Field of Classification Search
USPC .......................................... 424/725, 773, 489

IPC ....................................................... A61K 36/39
See application file for complete search history.

(56) References Cited

U.S. PATENT DOCUMENTS

| 2011/0165279 A1* | 7/2011 | Lin et al. ........................ 424/773 |
| 2012/0034342 A1* | 2/2012 | Courbois et al. ................ 426/48 |
| 2013/0017292 A1* | 1/2013 | Gellenbeck et al. .............. 426/2 |
| 2013/0095141 A1* | 4/2013 | Schad et al. ................... 424/400 |

FOREIGN PATENT DOCUMENTS

| CN | 1287811 A | * | 3/2001 |
| CN | 101411419 A | * | 4/2009 |
| CN | 102146360 | * | 8/2011 |
| CN | 103004717 A | * | 4/2013 |
| CN | 203411495 U | * | 1/2014 |

OTHER PUBLICATIONS

Hwang et al. J. Agric. Food Chem. 2007. vol. 55, No. 15, pp. 6000-6006.*

* cited by examiner

*Primary Examiner* — Chris R Tate
(74) *Attorney, Agent, or Firm* — WPAT, P.C.; Anthony King; Kay Yang

(57) ABSTRACT

The present invention relates to a micro-particle for extending satiety and controlling blood glucose and lipid levels, comprising a core having the protein extract from sweet potato, an active ingredient layer coated on the core, and a protection layer coated over the active ingredient layer as an external layer, wherein the protein extract from sweet potato contains trypsin inhibitor and glycoprotein. The micro-particle comprising a protein extract from sweet potato can effectively extend satiety, control blood glucose and lipid levels and increase metabolism effectively.

1 Claim, 4 Drawing Sheets

MICRO-PARTICLE COMPRISING A PROTEIN EXTRACT FROM SWEET POTATO FOR EXTENDING SATIETY AND CONTROLLING BLOOD GLUCOSE AND LIPID LEVELS

BACKGROUND OF THE INVENTION

1. Field of the Invention

The present invention relates to a micro-particle comprising a protein extract from sweet potato, especially relates to a micro-particle comprising a protein extract from sweet potato for extending satiety and controlling blood glucose and lipid levels.

2. The Prior Arts

People pay more attention to have a healthy body in recent years. In general, obesity is one of the major factors for unhealthy body, because obesity increases the likelihood of various diseases, particularly cardiovascular disease, hypertension, diabetes, fatty liver, endocrine disorders and certain types of cancer.

People are more concerned with producing satiety after eating a small amount or low calorie food to satisfy their appetites and achieve the slimming effect at the same time. The food producing satiety is dependent on the volume and the weight of the food, because the food with a larger volume can produce more satiety, such as cellulose, protein and moisture content in the food and the food with more quantity can also produce more satiety.

Therefore, the food or beverage in the market to produce satiety mainly is dietary fiber, that including polysaccharide and lignin cannot be digested and can absorb moisture in the digestive system. It can increase the food volume in stomach and intestines to produce satiety, such as, the food and beverage are made of Japan agar, konjac jelly and chicory fiber. The function of dietary fiber is to increase sense of fullness, to stimulate peristalsis in stomach and intestines, to reduce blood cholesterol and blood triacylglycerol and to prevent obesity. However, for people suffering from flatulence and indigestion, the increase of taking dietary fiber will lead to the side effect of delayed gastric emptying and suppressing mineral absorption. Moreover, dietary fiber tends to give people the impression of bad taste, and dietary fiber beverage is not easily to carry and to preserve, it must be finished off once opened.

Thus, it needs to improve above-mentioned disadvantages of dietary fiber beverage. Such that people can take a functional supplement for good health and achieve the purpose of extending satiety in a direct and convenient way.

SUMMARY OF THE INVENTION

To solve the above problems, in one aspect, the present invention relates to a micro-particle for extending satiety and controlling blood glucose and lipid levels, comprising a core having the protein extract from sweet potato, an active ingredient layer coated on the core, and a protection layer coated over the active ingredient layer as an external layer, wherein the protein extract from sweet potato contains trypsin inhibitor and glycoprotein, and the protein extract from sweet potato can be easily absorbed by gastrointestinal tract to achieve the effect of controlling blood glucose and lipid levels and increasing metabolism. The particle size of the micro-particle is in the range of 120 μm to 500 μm, the thickness of the core of the micro-particle is in the range of 30 μm to 150 μm, and the thickness of the active ingredient layer of the micro-particle is the in the range of 20 μm to 70 μm.

In another aspect, the core of the micro-particle of the prevent invention can further comprise oat fiber which is helpful to reduce the absorption of nutrients, to extend satiety and to control blood glucose and lipid levels.

In an alternative to another aspect, the active ingredient layer of the micro-particle is selected from the group consisting of a guarana extract, a bitter orange extract, L-cartinine, coenzyme Q10, fucoxanthin, probiotics, vitamin B6, vitamin B2, chromium picolinate, tryptophan, tyrosine, a banaba leaf extract, niacinamide and mixtures thereof, which all are helpful to extend satiety, to suppress appetite, to promote energy metabolism, to enhance blood glucose control and accelerate lipolysis.

In one preferred embodiment, the micro-particle of the present invention is employed as a healthy food or a pharmaceutical composition in an effective amount for extending satiety and controlling blood glucose and lipid levels. And the micro-particle of the present invention also can be filled in a capsule or in the form of a tablet, such as a two layer tablet, an effervescent tablet, a slow release tablet.

In another preferred embodiment, the micro-particle of the present invention can be in the form of powder or liquid.

The micro-particle of the present invention not only can provide a sense of fullness as general dietary fiber but also can be helpful to suppress appetite, to control blood glucose and lipid levels and to increase metabolism effectively. The micro-particle of the present invention can be a health supplement to improve the disadvantages of general dietary fiber beverage in carrying and preserving and to exhibit the best stability of bio-active ingredient. So that the general public can take the rich nutrition of the sweet potato in a direct and convenient way. The micro-particle of the present invention can extend the best consumed day of bio-active ingredient of the protein extract of sweet potato.

In the present invention, the micro-particle can achieve the effect to produce a feeling of fullness, to decrease appetite and caloric intake, to lose weight, to lower body mass index (BMI) and blood lipid (including triacylglycerol and cholesterol) and to stimulate the body burning calories.

The present invention is further explained in the following embodiment illustration and examples. Those examples below should not, however, be considered to limit the scope of the invention, it is contemplated that modifications will readily occur to those skilled in the art, which modifications will be within the spirit of the invention and the scope of the appended claims.

DETAILED DESCRIPTION OF THE PREFERRED EMBODIMENT

Figure 1:
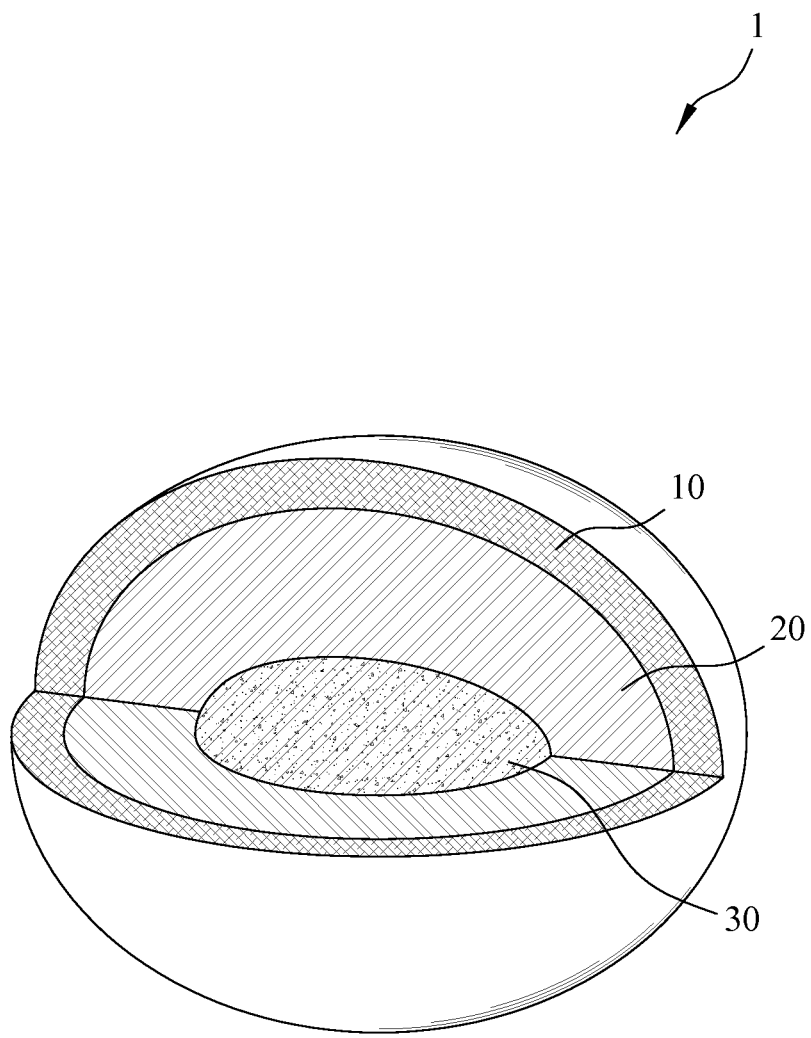
FIG. 1 is a sectional view of a preferred embodiment of the present invention.

The present invention is a micro-particle comprising a protein extract from sweet potato for extending satiety and controlling blood glucose and lipid levels. The foregoing aspects and many of the accompanying advantages of this invention will become more readily appreciated as the same becomes better understood by reference to the following detailed description when taken in conjunction with the accompanying drawings. As shown in FIG. 1, it is a sectional view of a preferred embodiment of the present invention. In the embodiment, the micro-particle is a spheroid, and it is not intended to limit the scope of the present invention. The micro-particle 1 of present invention, which comprises a protection layer 10, an active ingredient layer 20, and a core 30 having a protein extract from sweet potato, wherein the core 30 having a protein extract from sweet potato is extracted and purified by special technology, the protein extract contains natural trypsin inhibitor and glycoprotein to achieve the effect of extending satiety and lowering blood lipid.

The particle size of the micro-particle 1 of the present invention is in the range of 120 μm to 500 μm, the thickness of the core 30 having a protein extract from sweet potato of the micro-particle is in the range of 30 μm to 150 μm, and the thickness of the active ingredient layer 20 of the micro-particle is the in the range of 20 μm to 70 μm.

The sweet potato (Ipomoea batatas) is a dicotyledonous plant that belongs to the family Convolvulaceae, and it is kind of food good for health. The sweet potato comprises dietary fiber, carotene, vitamin A, vitamin B, vitamin C, vitamin E, potassium, iron, copper, selenium, calcium and more than 10 kinds of trace elements. Thus, it is a well-known nutrient-rich food.

In the present invention, the protein extract from sweet potato is extracted and purified by special technology, and the protein extract has natural trypsin inhibitor and glycoprotein, which can stimulate small intestine to release cholecystokinin (CCK). CCK is a gastrointestinal hormone which regulates gastric motility, it is released following the consumption of food, and it binds to CCK-A receptor in both the liver and the central nervous system transmitting the satiety signals to the brain, Therefore, the micro-particle of the present invention can extend the satiety and decrease food intake. In addition, the protein from sweet potato can active peroxisome proliferators activated receptor (PPAR) in fat cells to lower blood lipid (including triacylglycerol and cholesterol) and can increase leptin released from fat cells to suppress appetite and to increase calorie burn. With CCK releasing, the micro-particle of the present invention can achieve the effect of controlling body weight through reducing food intake and burning calories.

In the present invention, the protein extract from sweet potato is extracted and purified by special technology as following steps: put the cleaned and peeled sweet potato into the saw tooth grinding machine to grind sweet potato into mud like, put the sweet potato mud into homogeneous machine to make it become uniform particles, put the sweet potato particles on the ice and add 1% to 5% acetic acid to reach a pH of 4 and 1% to 10% sodium chloride to extract trypsin inhibitor, separate precipitate and liquid of sweet potato from the preceding step by using horizontal centrifuge (1,500 rpm to 2,500 rpm), obtain the sweet potato liquid containing the desired trypsin inhibitor and glycoprotein, heat the sweet potato liquid up to 72° C. to 80° C. to remove other components except trypsin inhibitor, put the sweet potato liquid on ice to cool down the sweet potato liquid to 20° C. to 25° C., remove tiny particle from the sweet potato liquid using filtration membrane and remove the larger molecular weight of organic molecule from the preceding sweet potato liquid using microfiltration membrane, obtain a target protein with molecular weight of 20 KD to 200 KD. The target protein is the protein extract from the sweet potato in present invention; it can maintain and stabilize bio-activity after lyophilizaion.

Referring to FIG. 1, the core 30 of the micro-particle in the prevent invention can further comprise oat fiber. In one embodiment, weight ratio of oat fiber to the protein from sweet potato is 3:1 to 1:10. Oat fiber is helpful to reduce the absorption of carbohydrate and fat, to extend satiety and to control blood glucose and lipid levels.

As shown in FIG. 1, the active ingredient layer 20 of the micro-particle in the prevent invention is selected from the group consisting of a guarana extract, a bitter orange extract, L-cartinine, coenzyme Q10, fucoxanthin, probiotics, vitamin B6, vitamin B2, chromium picolinate, tryptophan, tyrosine, a banaba leaf extract, niacinamide and mixtures thereof, which all are helpful to extend satiety, suppress appetite, promote energy metabolism, enhance blood glucose control and accelerate lipolysis.

The object of extending satiety, bitter orange is a kind of citrus, and bitter orange extract contains a component binding to adrenergic β-3 receptor, the component not only can promote hypothalamus in central nervous system to produce satiety but also can increase the speed of metabolism. In addition, tryptophan (Trp) is the precursor of 5-hydroxytryptamine (5-HT), and it has been reported that the increase of 5-HT in the brain can suppress appetite and produce satiety, vitamin B6 plays in facilitating Trp conversion to 5-HT, so both of bitter orange and vitamin B6 have the effect of extending satiety and suppressing appetite.

The object of promoting energy metabolism, it has been known that mitochondria are dynamic organelles fundamental for cell life, there are uncoupling proteins (UCP-1) in the electron transport chain of the mitochondrial inner membrane. Fucoxanthin is shown to increase UCP-1 concentration in white adipose tissue, which is the reason it's effective for burning off excess fat and reducing obesity. L-carnitine is needed to transport long-chain fatty acids into a cell's mitochondria to produce energy. Coenzyme Q10 is one of several important mitochondrial enzymes required for electron transport, and is thus a critical part of the process of generating energy within cells. Niacinamede is in form of NADH (Nicotinamide adenine dinucleotide), it is the general electron carrier funneling electrons into the mitochondrial electron transport chain for oxidative phosphorylation to promote energy metabolism.

The object of enhancing blood glucose control, chromium picolinate works with insulin in assisting cells to take in glucose and release energy, it can significantly improve glucose intolerance and reduce blood sugar and insulin levels in those with diabetes. Banaba leaf extract stimulates the transport of glucose into cells resulting in lower blood glucose levels, it may aid weight loss when used as an appetite suppressant to control food cravings and may be used in the treatment of immune system.

The object of accelerating lipolysis, guarana extract has nature coffenine, it can break down triglycerides into free glycerol and fatty acids. In addition, oat fiber is helpful to reduce the absorption of nutrients, to extend satiety and to control blood glucose and lipid levels. Probiotics are beneficial bacteria and yeast that promote healthy digestion and immunity, and it can accelerate the metabolism of lipid, starch, and protein and can be helpful to eliminate waste, to loss weight and to lower glucose level.

In one embodiment, the total weight of the micro-particle of the present invention is 1,500 mg, which contains approximately or above 10% of the protein extract from sweet potato, approximately 30% of oat fiber, approximately or above 2% of L-carnitine, approximately or above 6% of probiotics, approximately 0.006% of vitamin B2, approximately or above 10% of tryptophan, approximately or above 20% of tyrosine, and approximately or above 0.002% of niacinamide.

In another embodiment, the total weight of the micro-particle of the present invention is above 1,500 mg, which contains approximately 30% to 50% of the protein extract from sweet potato, approximately 3% to 35% of oat fiber, approximately 3% of a guarana extract, approximately 3% of a bitter orange extract, approximately 5% to 10% of L-carnitine, approximately 1% of coenzyme Q10, approximately 8% to 12% of fucoxanthin, approximately 3% to 6% of probiotics, approximately 0.1% of chromium picolinate, approximately 0.133% of vitamin B6, approximately 0.067% of vitamin B2, approximately 10% of tryptophan, approximately 0.9% of a banaba leaf extract and approximately 0.8% of niacinamide.

In one embodiment, as shown in FIG. 1, the protection layer 10 of the micro-particle in the present invention is selected from the group consisting of edible gels such as gelatin, Arabic gum, xanthan gum and tragacanth gum. In another embodiment, the protection layer 10 the micro-particle in the present invention further comprises an excipient, wherein the excipient is selected from the group consisting of a flavoring agent, a sweetener, a preservative, an anti-oxidant, a chelator, a permeation enhancer, a lubricant, a colorant and a bonding agent.

In another embodiment, as shown in FIG. 1, the protection layer 10 of the micro-particle in the present invention is film coating protection layer is made from a film coating process, which comprises sugar-coating, enteric membrane-controlled release coating, water-soluble clear coating, yellow film coating or combinations thereof. The micro-particle in the present invention can keep the surface smooth after administering orally, which can prevent to stick in the oral cavity or esophagus and to destroy gastrointestinal.

One embodiment of the present invention is that the protection layer 10 is a water-soluble clear coating (in FIG. 1). The water-soluble clear coating comprises a cellulosic polymer, a synthetic polymer and a polysaccharide. The cellulosic polymer may be hydroxypropyl cellulose, hydroxypropyl methyl cellulose, hydroxypropyl methyl cellulose, methyl hydroxyethyl cellulose and the like. The synthetic polymer may be polyvinylacetal diethylaminoacetate, aminoalkyl methacrylate copolymer E, polyvinyl pyrrolidone and the like. The polysaccharide may be triglucoside and the like.

Another embodiment of the present invention is that the protection layer 10 is an enteric membrane-controlled release coating (in FIG. 1). The enteric membrane-controlled release coating is dissolved only when entering into the intestine environment and subsequently releasing the bioactive compositions of the core layer, such that these bioactive ingredients will not be destroyed by the gastric acid. The enteric membrane-controlled release coating comprises castor oil, shellac, mineral oil, 1,2-propandiol, polymethylmethacrylate, triethyl citrate, tributyl citrate, dimethyl phthalate, diethyl phthalate, polyethyleneglycol, cellulose acetate phthalate, hydroxypropylmethyl cellulose phthalate, hydroxypropyl methylcellulose or combinations thereof.

Thus, the present invention relates to a micro-particle comprising a protein extract from sweet potato for extending satiety and controlling blood glucose and lipid levels, referring to FIG. 1, the protection layer 10 is coated over all the active ingredient layer 20 and core 30 having the protein extract from sweet potato, which can prevent the bio-active ingredient from contamination and deterioration, such that the micro-particle of the present invention can extend and keep the bio-activity of the protein extract from sweet potato. Furthermore, the protein extract from sweet potato is not destroyed by the digestive enzymes in the gastrointestinal tract and is helpful to be absorbed.

Figure 2:
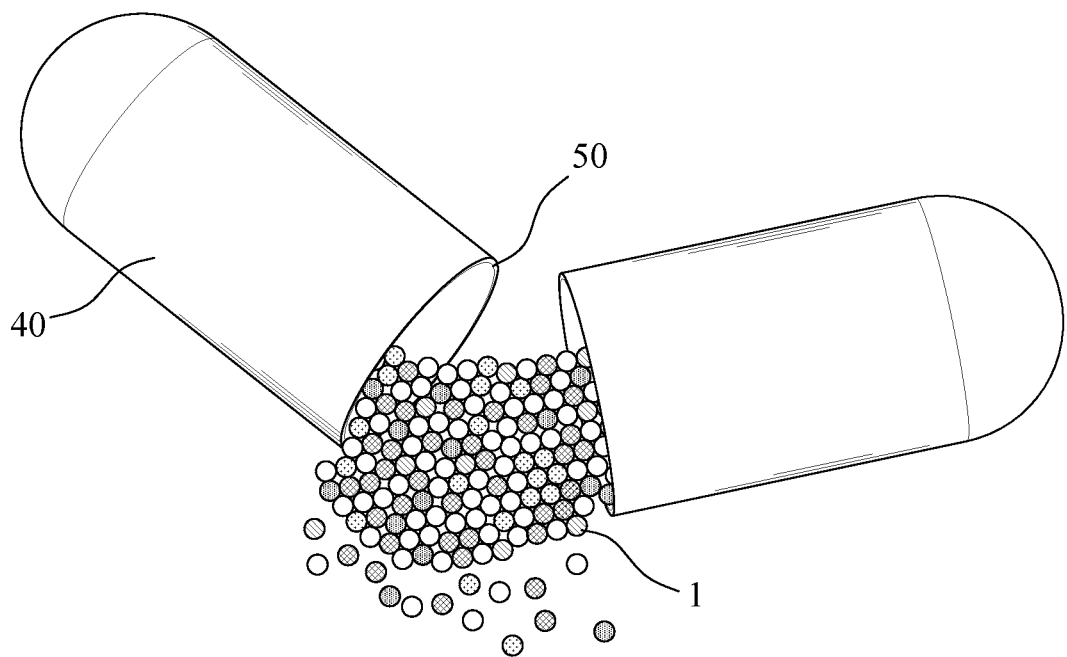
FIG. 2 is a schematic diagram of a preferred embodiment of the present invention pre-filled in a capsule.

In a preferred embodiment of the present invention, the micro-particle can be pre-filled in the form of a capsule. As shown in FIG. 2, the capsule container 40 is made from edible gelatin, and they are made up of a rigid shell 50 in two pieces that fit together and the rigid shell is filled with the micro-particle 1 of the present invention.

Figure 3:
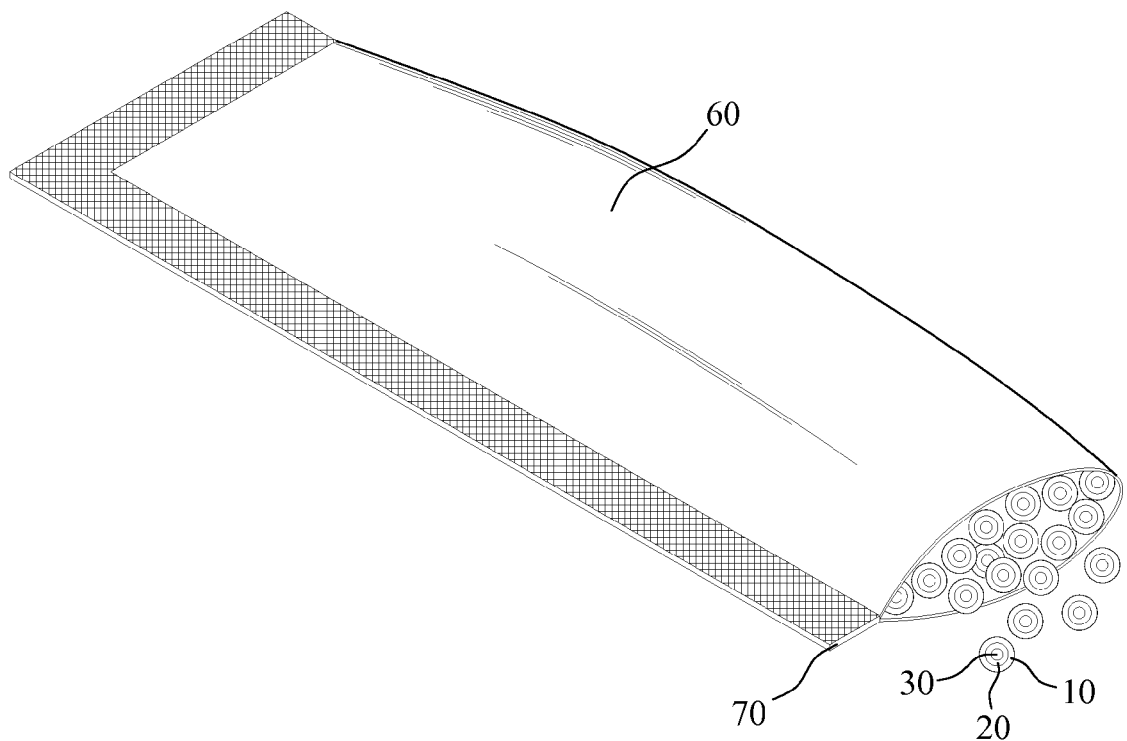
FIG. 3 is a schematic diagram of a preferred embodiment of the present invention filled in a packet.

In a preferred embodiment of the present invention, the micro-particle can be made into a functional beverage easily by dissolving in water or administered orally. As shown in FIG. 3, the micro-particle 1 of the present invention is filled in a packet 60, and people can simply tear off the top of the stick 70 and directly take the micro-particle 1 into mouth, and the micro-particle 1 comprises a core 30 having a protein extract from sweet potato, an active ingredient layer 20 and a protection layer 10.

Figure 4:
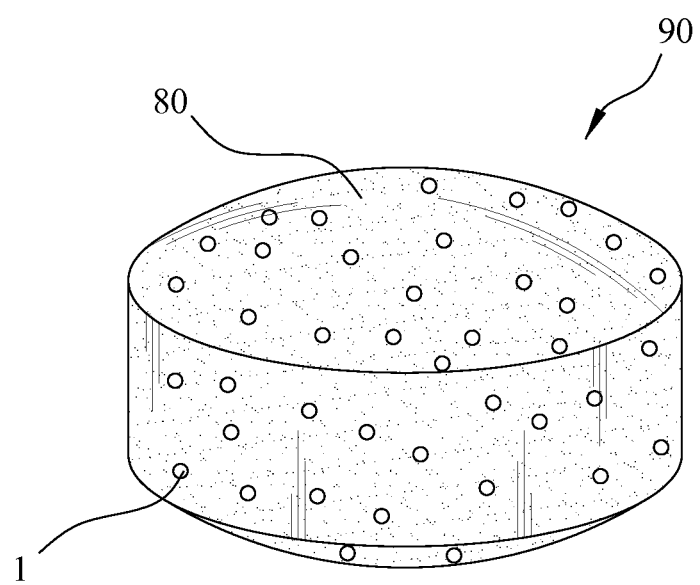
FIG. 4 is a schematic diagram of a preferred embodiment of the present invention pressed into a tablet.

In a preferred embodiment of the present invention, the micro-particle can be in the form of a tablet, which can be supplemented with lactose, starch or cellulose to make a two layer tablet, or can be supplemented with citric acid, malic acid, and sodium bicarbonate to make an effervescent tablet, or can be supplemented with slow release component to make a slow release a tablet. As shown in FIG. 4, a plurality of the micro particle 1 of the present invention spreads evenly over the tablet base 80 to make a tablet 90, and it can be a healthy food or a pharmaceutical composition.

In a preferred embodiment of the present invention, testers take one packet 60 (FIG. 2) on an empty stomach 30 mins before food in the morning for 45 to 60 days, and testers have significantly improvement in weight, appetite, abdominal fat and cholesterol.

In summary, the present invention is a micro-particle comprising a protein extract from sweet potato, and the protein extract containing natural trypsin inhibitor and glycoprotein is extracted and purified by special technology to achieve the effect of extending satiety and reducing food intake. And the micro-particle of present invention also comprises other components to achieve the effect of producing a feeling of fullness, decreasing appetite and caloric intake, losing weight, lowering body mass index (BMI) and blood lipid (including triacylglycerol and cholesterol) and stimulating the body burning calories. In addition, the micro-particle of present invention can dissolve in water quickly, and the protein extract containing natural trypsin inhibitor and glycoprotein can be absorbed directly into the blood stream after drinking and can increase speed of the absorption effectively. The micro-particle of present invention can make those fat population reduce hunger and food intake, block carbohydrate and fat absorption, increase calorie burn, such that it can completely achieve the best effect of body slimming. Moreover, the micro-particle of present invention can be given people in variety of formulations, which increase the consumer choice and convenience. Therefore, the micro-particle of present invention is a functional supplement for good health.

What is claimed is:

1. A method for obtaining a trypsin-inhibiting protein extract from a sweet potato comprising:
   a. grinding a cleaned and peeled sweet potato in a saw tooth grinding machine;
   b. homogenizing the ground sweet potato in a homogenizing machine to form sweet potato particles of uniform size,
   c. placing the sweet potato particles on ice to cool the sweet potato particles, and adding 1% to 5% acetic acid and 1% to 10% sodium chloride to the cooled sweet potato particles to obtain a crude extract;

d. centrifuging the crude extract in a horizontal centrifuge to form a liquid extract and a precipitate;
e. removing the precipitate from the centrifuged extract to obtain the liquid extract, wherein the liquid extract has trypsin-inhibitory activity;
f. heating the obtained liquid extract to a temperature of 72° C. to 80° C.;
g. placing the heated liquid extract on ice to cool it down to a temperature of 20° C. to 25° C.;
h. filtering the cooled liquid extract through a filtration membrane to remove tiny particles from the liquid extract, and
i. passing the filtered liquid extract obtained in step h through a microfiltration membrane to obtain said trypsin-inhibiting protein extract, wherein the protein molecules within the protein extract have a molecular weight of 20 KD to 200 KD.

\* \* \* \* \*